(12) United States Patent
Marka et al.

(10) Patent No.: US 8,134,309 B2
(45) Date of Patent: Mar. 13, 2012

(54) LAMP POWER TABULATION

(75) Inventors: Rudolf Marka, Ismaning (DE); Markus Vogl, Weilheim (DE)

(73) Assignee: Trumpf Medizin Systeme GmbH + Co. KG, Saalfeld (DE)

(*) Notice: Subject to any disclaimer, the term of this patent is extended or adjusted under 35 U.S.C. 154(b) by 1302 days.

(21) Appl. No.: 11/559,584

(22) Filed: Nov. 14, 2006

(65) Prior Publication Data
US 2007/0138966 A1 Jun. 21, 2007

(30) Foreign Application Priority Data
Nov. 14, 2005 (EP) .................................. 05024819

(51) Int. Cl.
*H05B 37/00* (2006.01)
(52) U.S. Cl. ......... 315/312; 315/294; 315/307; 362/227
(58) Field of Classification Search .............. 315/149, 315/185 R, 291, 294, 297, 307–309, 312; 362/277, 231, 262, 263
See application file for complete search history.

(56) References Cited

U.S. PATENT DOCUMENTS

| | | | |
|---|---|---|---|
| 3,588,488 A | 6/1971 | Lauterbach | |
| 3,930,149 A | 12/1975 | French | |
| 4,196,460 A * | 4/1980 | Schreckendgust | 362/231 |
| 4,380,794 A | 4/1983 | Lawson | |
| 4,757,426 A | 7/1988 | Scheller et al. | |
| 6,488,390 B1 | 12/2002 | Lebens et al. | |
| 6,495,964 B1 | 12/2002 | Muthu et al. | |
| 6,582,092 B1 | 6/2003 | Marka | |
| 6,636,003 B2 | 10/2003 | Rahm et al. | |
| 6,744,223 B2 * | 6/2004 | Laflamme et al. | 315/291 |
| 6,759,814 B2 * | 7/2004 | Vogel et al. | 315/312 |
| 6,788,011 B2 | 9/2004 | Mueller et al. | |
| 6,880,957 B2 | 4/2005 | Walters | |
| 7,014,336 B1 | 3/2006 | Ducharme et al. | |
| 7,038,399 B2 * | 5/2006 | Lys et al. | 315/291 |
| 7,042,172 B2 * | 5/2006 | Dowling et al. | 315/294 |
| 7,145,125 B2 | 12/2006 | May et al. | |
| 7,202,613 B2 * | 4/2007 | Morgan et al. | 315/312 |
| 7,221,104 B2 * | 5/2007 | Lys et al. | 315/291 |

(Continued)

FOREIGN PATENT DOCUMENTS
DE 19838627 3/2000
(Continued)

OTHER PUBLICATIONS
English translation of Office Action from corresponding Chinese Application No. 200610171942.1 dated Mar. 10, 2009, 3 pages.
(Continued)

*Primary Examiner* — Tung X Le
(74) *Attorney, Agent, or Firm* — Fish & Richardson P.C.

(57) ABSTRACT

An operating lamp includes a plurality of illumination elements arranged in discrete groups. The illumination elements include at least one white illumination element, adapted to emit a white light, and multiple colored illumination elements, each adapted to emit a non-white, colored light. The operating lamp also includes a controller in communication with the illumination elements, and one or more storage devices configured to communicate with the controller. Each of the storage devices is associated with one or more of the groups of illumination elements, and each of the storage devices contains a set of power values for each associated group. The controller is configured to control illumination of each group of illumination elements individually, based on the associated power values.

25 Claims, 3 Drawing Sheets

U.S. PATENT DOCUMENTS

| | | | |
|---|---|---|---|
| 7,614,763 B2 | 11/2009 | Leibinger et al. | |
| 7,828,459 B2* | 11/2010 | Rains | 362/231 |
| 2001/0021108 A1 | 9/2001 | Shimada et al. | |
| 2002/0048177 A1 | 4/2002 | Rahm et al. | |
| 2002/0085390 A1* | 7/2002 | Kiyomoto et al. | 362/555 |
| 2003/0165055 A1 | 9/2003 | Scholz | |
| 2003/0185009 A1 | 10/2003 | Walters | |
| 2004/0129860 A1 | 7/2004 | Thibaud et al. | |
| 2004/0160199 A1* | 8/2004 | Morgan et al. | 315/312 |
| 2005/0195599 A1 | 9/2005 | Marka | |
| 2005/0231945 A1 | 10/2005 | Leibinger et al. | |
| 2006/0082987 A1* | 4/2006 | Dorsey et al. | 362/103 |
| 2006/0158881 A1* | 7/2006 | Dowling | 362/231 |
| 2006/0187081 A1* | 8/2006 | Gloisten et al. | 340/825.22 |
| 2010/0148689 A1* | 6/2010 | Morgan et al. | 315/250 |

FOREIGN PATENT DOCUMENTS

| | | |
|---|---|---|
| DE | 10034594 | 1/2002 |
| DE | 10216645 | 11/2003 |
| EP | 1462711 | 9/2004 |
| EP | 1568936 | 8/2005 |
| EP | 1568938 | 8/2005 |
| JP | 11178839 | 6/1999 |
| JP | 2003518323 A | 6/2003 |
| WO | WO 99/22224 | 5/1999 |
| WO | WO0035402 | 6/2000 |
| WO | WO0136864 | 5/2001 |
| WO | 0146617 A1 | 6/2001 |
| WO | WO03019072 | 3/2003 |
| WO | WO03096761 | 11/2003 |

OTHER PUBLICATIONS

HIT-Colorlite: Metal-halide lamps in green, blue, magenta and orange, BLV Produktkatalog 2004/2005, 1 page.

Halogen Gluehlampen, BLV-USHIO Group, 2006, 11 pages.

"Metalldampflampe", from Wikipedia, Jan. 7, 2007, 2 pages, http://de.wikipedia.org/wiki/Metalldampflampe—English equivalent is "Gas-discharge Lamp", also from Wikipedia, http://en.wikipedia.org/wiki/Gas-discharge_lamp.

Notice of Opposition of Brandon Medical Ltd. as filed in the European Patent Office, filed Jun. 21, 2007, 23 pages.

Notice of Opposition of Berchtold Holding GmbH, including English translation, dated Jun. 26, 2007, 30 pages.

Notice of Opposition of Dr. Mach GmbH & Co. KG, including English translation, dated Jun. 27, 2007, 52 pages.

Reply of Patent Proprietor to Notice of Opposition, dated Mar. 20, 2008, 46 pages.

Annex to Search Report of European Patent Application No. 04 004 602.1, in German language with English translation, mailed Jun. 30, 2004, 7 pages.

\* cited by examiner

LAMP POWER TABULATION

RELATED APPLICATION

Under 35 U.S.C. §119, this application claims the benefit of a foreign priority application filed in Europe, serial number EP 05 024 819.4, filed Nov. 14, 2005, the entire contents of which are hereby incorporated by reference.

TECHNICAL FIELD

This disclosure relates to controlled illumination of an operating lamp, e.g., for illuminating an operating area.

BACKGROUND

Control of a luminous flux of an operating lamp with respect to color temperature, intensity and distribution over a light emitting surface can be realized with operating lamps having conventional illumination means, such as halogen or gas discharge lamps. A color temperature of halogen or gas discharge illumination means can be adjusted, for example, using filter techniques. The color temperature can also be changed when several illumination means are used. Brightness can be adjusted using apertures, e.g., without changing the color temperature. With electric dimming, a change in brightness can also change the color temperature. In addition, distribution of the luminous flux over a light emitting surface can be changed through aperture techniques and/or with the use of several illumination means.

It is desired to improve activating of illumination means of an operating lamp with respect to adjustment of a color temperature and an intensity (brightness) of the operating lamp.

SUMMARY

According to one aspect, individual illumination means (i.e., illumination elements) are combined into groups. Power values, which are allocated with the groups, are stored (e.g., on a corresponding storage device) so that a controller can drive these groups separately.

A color temperature and intensity (brightness) of operating lamps can be adjustable. Towards this end, light emitting diodes (LEDs) of different colors (e.g., cold white, warm white, cyan, blue) can be used as illumination elements. The illumination elements, and/or individual groups of the illumination elements, can then be driven by adjustable power values (e.g., current and/or voltage). In order to standardize illumination parameters for individual groups of the illumination elements, power values for different illumination parameters are stored for each group.

A color temperature of the operating lamp, a light intensity of the operating lamp and/or a distribution of the light intensity across a light emitting surface of the operating lamp can be taken into consideration as nominal values for the illumination parameters. The groups of illumination elements can be driven, controlled and calibrated using the nominal values.

A current strength can be used as a power value or luminous flux value. The current strength can be controlled by the nominal values. A current value can be used to control the current strength. Alternatively or additionally, the current value can be a pulse sequence for pulse width modulation. The illumination elements can be combined into one or more modules or combinations. This provides the possibility to design different operating lamps.

Each module or each combination can include a corresponding storage device (e.g., an EPROM). Moreover, data transfer to a central controller of the operating lamp can be provided. This can help to facilitate exchange of modules for repair work. For example, by storing the data for each nodule, a replacement module can be installed which has the same lighting properties. Even after replacement of the central controller, operation of the lamp with its calibrated values is ensured.

The details of one or more embodiments of the invention are set fourth in the accompanying drawings and the description below. Other features, objects, and advantages of the invention will be apparent from the description and drawings, and from the claims.

DETAILED DESCRIPTION

Figure 1:
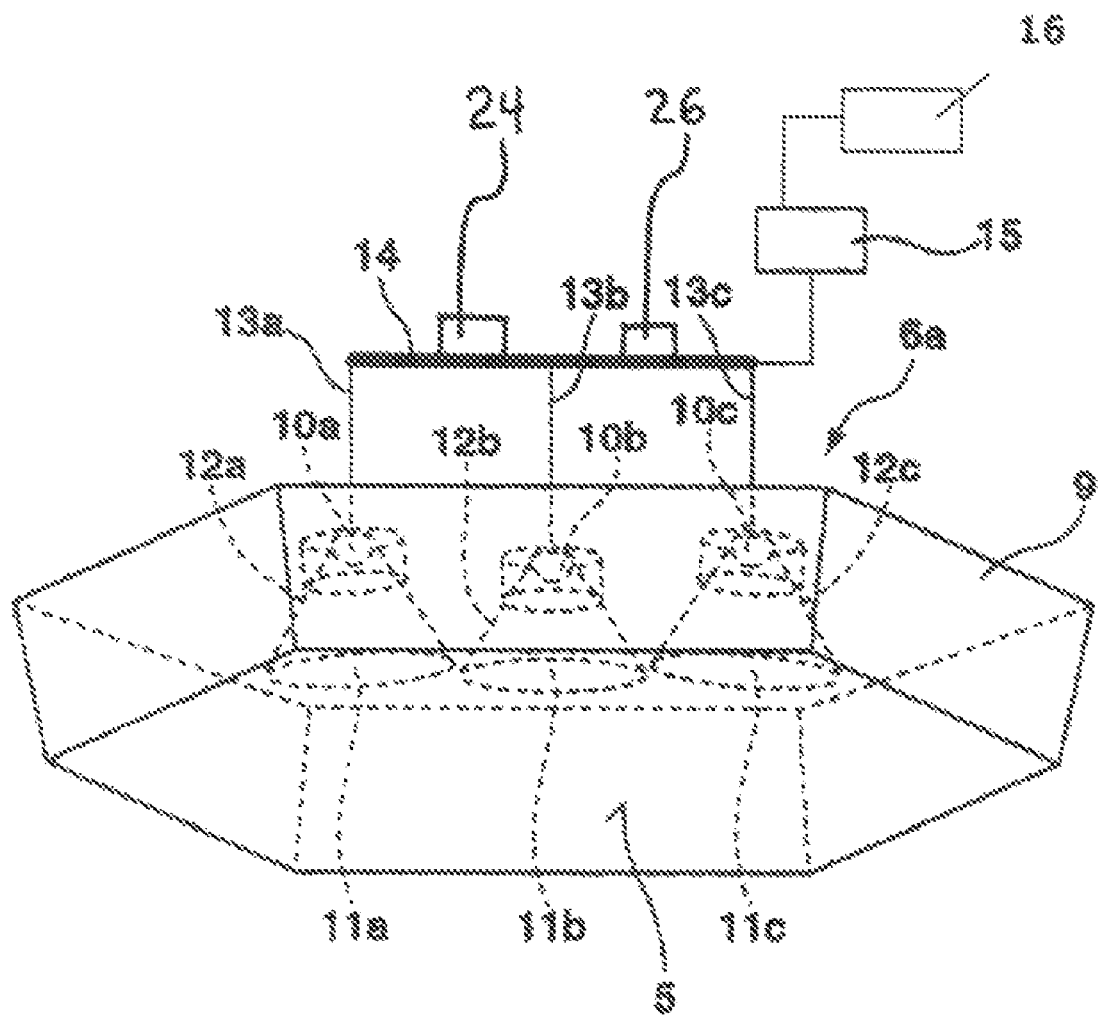
FIG. 1 shows an embodiment of a light module for an operating lamp.

As shown in FIG. 1, an individual light module 6a can include a housing 9 having mechanical and/or electric or electronic connecting elements or connectors, e.g., for connecting the module to neighboring light modules. The shape of the light module is designed such that a plurality of the modules can be disposed on a curved (e.g., spherical) surface. For example, in some embodiments a plurality of the modules are disposed on a surface having a radius of 1000 mm without substantial gaps between adjacent modules. Towards this end, the light modules can have a hexagonal shape, such that, when assembled, a type of honeycomb or facette structure is formed. The surface of the light modules need not necessary be flat, but may be slightly concave to improve reproduction of the curvature of the spherical surface, and an optical axis of the light module 6a can face a focus of the spherical surface.

Different light field shapes can be generated by combining light from adjacent modules oriented at different angles of incidence. Intermediate elements can also be used in this connection. Multiple (e.g., 10, 20, 30, 40, 50 or more) LEDs can be uniformly distributed, in the light module 6a, of which only three (i.e., 10a-10c) are shown in FIG. 1. Formation of shadows is optimized through planar emission of light from the LEDs 10a-10c. Toward this end, each of the nearly point source LEDs 10a-10c can be associate with suitable optical elements (e.g., lenses 11a-c), such that light beams 12a-c are emitted from the LEDs 10a-c, respectively. The shape of the optical elements 11a-c is designed such that they fill the light module 6a up to the edge thereof. The lens elements 11a-c can also have a scattering structure to render the illumination field more homogeneous. The lower side 5 of the light module 6a can be covered by a transparent plate.

Figure 2:
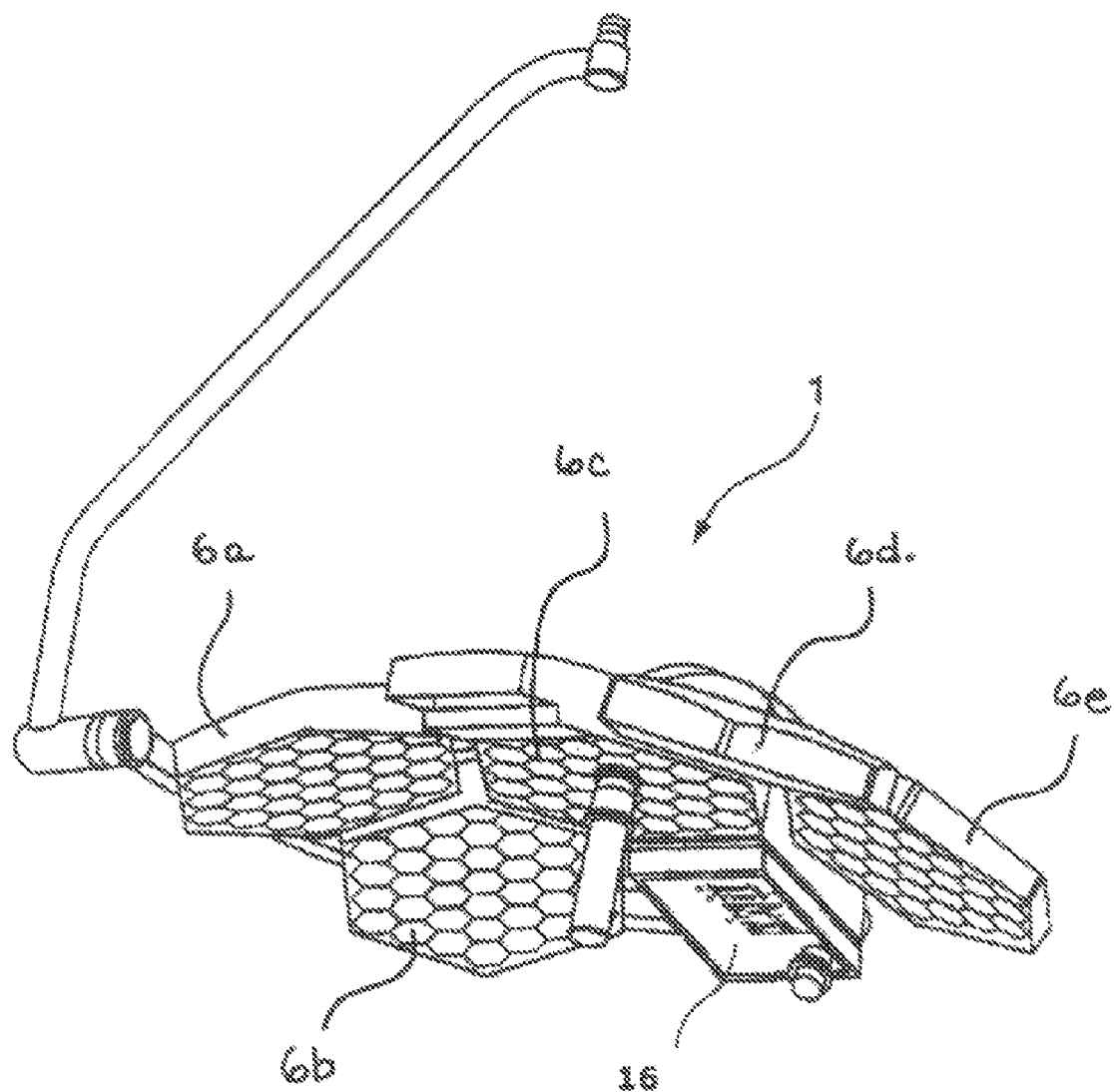
FIG. 2 shows one embodiment of an operating lamp.

The combination of individual light modules 6a-6e, as shown in FIG. 2, can form a light source having various color temperatures, for example, approximately 4500 K, and a color reproduction index Ra of greater than about 93 to obtain natural color representation of an illuminated object (e.g., tissue to be operated on). For this reason, LEDs (e.g., LEDs 10b and 10c) that generate colored (i.e., non-white) light are used in combination with white-light LEDs (e.g., LED 10a). The addition of colored light, such as cyan and blue, can help to minimize a spectral breakdown that can occur when only white-light LEDs are used. Moreover, specific color mixtures can be generated to improve the vision of the operating surgeon. With a constant brightness of the white LEDs in the light source, the color temperature and color reproduction of the mixed light, which is generated by the overall light source, consisting of all individual light modules 6a-6e can be variably adjusted. The luminous flux intensity of the LEDs 10a through 10c can be continuously changed by selectively dimming the intensity of the colored LEDs 10b and 10c. The overall illumination strength can also be kept constant through matched intensity control of all LEDs. The LEDs 10a-c can be connected to a central controller 15 through current lines 13a-c and printed board 14. This interconnect between the LEDs and the controller allows for electric dimming of the luminous flux of the LEDs, which can be selectively operated, e.g., through an operating element 16.

As shown in FIG. 2, a variably controlled operating lamp 1 can include a plurality of individual light modules 6a-6e, e.g., three or five or more. Each individual light module can include a plurality of (e.g., 35 or more) illumination elements (e.g., LEDs) of different colors. For example, in some cases, each individual LED, including its optical system, is able to illuminate the entire illumination field, and consequently also each individual light module 6a-6e. Different light intensities and/or color temperatures of the operating lamp can be adjusted, for example, by activating the LEDs in different ways. Thus, the individual light modules can be adjusted to achieve substantially identical optical effects, such as brightness and color temperature.

The LEDs can be combined into groups, wherein each group can be individually driven. The LEDs can be grouped, for example, according to color and, when the maximum current carrying capacity of the controller 15 has been exceeded, the number of LEDs. The individual groups can be combined in modules or other combinations. The groups can then be driven through the central controller 15 allowing a user can select a desired color temperature, light intensity, and/or distribution of the emitted light. The light intensity and/or color temperature of each module 6a-6e, or each combination of individual groups of LEDs, can be measured and calibrated to corresponding nominal values. This can also compensate for changes in the color temperature of the LEDs that occurs as result of dimming, i.e., as a result of a reduced current flow (linear current control). Calibration can also be used to compensate for variances in color temperature and light intensity, which can occur as a result of production tolerances of LEDs. Specifically, the power values for the individual groups can be measured and adjusted to achieve the nominal values. The resulting power values (i.e., the power values for reaching the nominal values)—are stored for the module 6a-e or the combination of individual groups. The power values correspond to the power at which each individual group can be driven in order to reach the set nominal values. This power value can be a current value (linear current control) or a pulse sequence for pulse width modulation for the supply current of the LEDs. The combination of the setting for the individual groups then yields the desired settings for the nominal values of color temperature, intensity and distribution. It is also possible not to store the power values but to measure the color temperature and intensity of the emitted light during operation and control the parameters therewith. The power values can be stored in the central controller 15. The power values can also be stored on individual storage devices 24 associated with corresponding module 6a-6e or combination of groups. This may be realized, e.g., on the printed board 14 in the module 6a-6e, on which the plug connector is disposed to distribute the electric supply. For example, a dedicated storage component 24 (FIG. 1), e.g., an EEPROM (electrically erasable programmable read-only memory) or a flash memory can be allocated to each module 6a-6e or combination of groups. When the operating lamp 1 is started, these values are transferred to the central controller 15 and the module 6a-6e or the combination is operated with the corresponding calibrated values.

Each module 6a-6e can also include a temperature sensor 26 to measure a temperature in the housing 9 and to reduce the light intensity in the event that the temperature is above a predetermined threshold temperature, thereby reducing the temperature.

A basic setting of a color temperature of 4500 K can be predetermined for the operating lamp 1 and automatically generated when the operating lamp 1 is switched on. Other desired color temperatures, depending on the application of the operating lamp 1, can be adjusted through the operating element 16 (e.g., control panel or user interface). The operating element 16 of FIG. 3 has a removable key/rotational switch 17, which can be sterilized. The switch 17 is actuated to send pulses to the controller for selecting different operating states and/or operating parameters. For example, the different operating states (outlined below) are sequentially switched through by pressing the switch 17:

on/off (complete switch-off or standby state)
light intensity (brightness)
color temperature
illumination situation (selection of the intensity distribution of the emitted light)
optional: camera drive (orientation, zoom)

Figure 3:
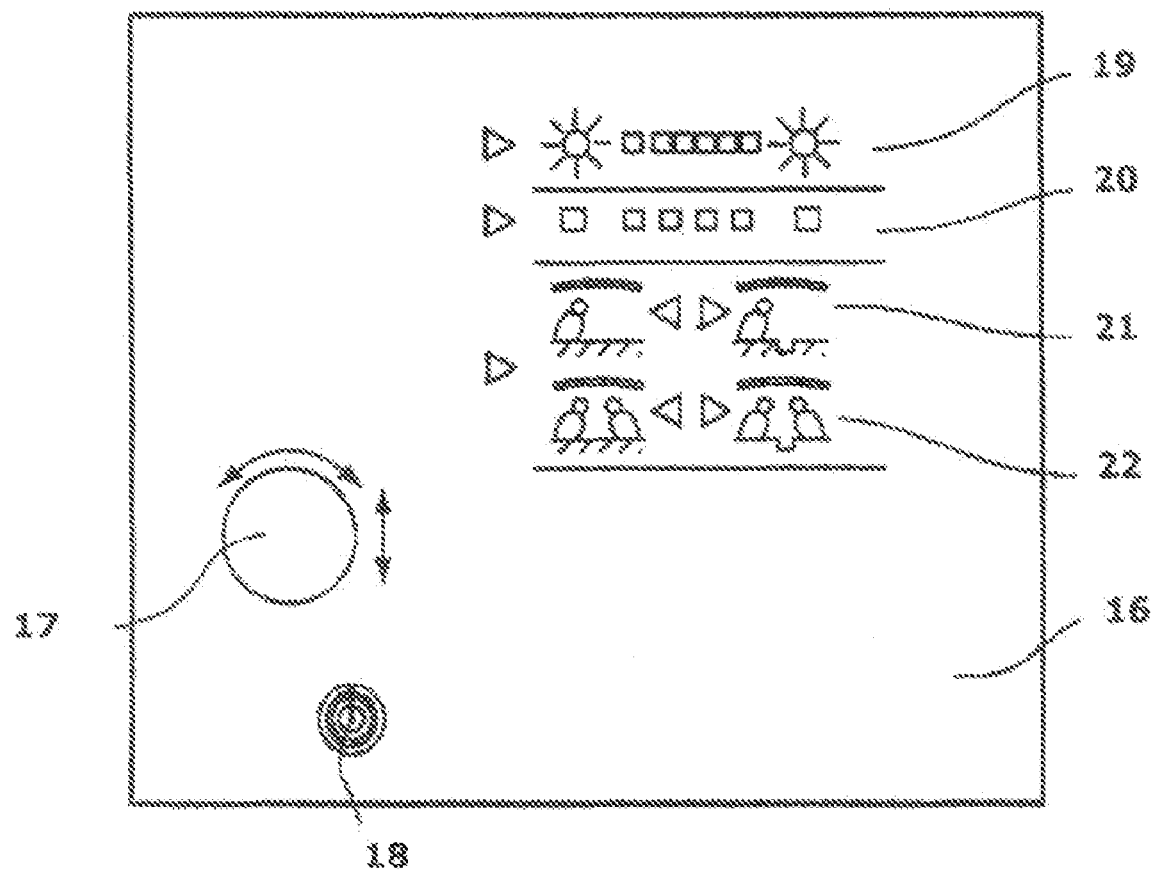
FIG. 3 shows an operating field of an operating element (i.e., user interface) for the operating lamp of FIG. 2.

Defined progressive rotation of the switch 17 is facilitated by latching positions. This changes the operating parameters (outline below) within the operating states. The different operating states and operating parameters can be displayed on the operating element 16. The following parameters are stored in the controller 15:

Light intensity: e.g. endo (10%)/50%/60%/70%/80%/90%/100%
Color temperature: e.g. 3500 K/4000 K/4500 K/5000 K
Illumination situation: e.g. 1 operating surgeon/2 operating surgeons/large-surface wound/deep narrow wound When the sterile switch 17 is switched off or on, the standby mode is activated or deactivated. The operating parameters are stored during switching off, and may be further displayed. When the operating lamp 1 is switched on, it assumes the operating state of the last stored parameters. The operating element 16 can include, in addition to the switch 17, a further switch 18 for completely switching the operating lamp on or off. When the operating lamp is switched on, it is in a state of predefined parameters (basic position). As shown in FIG. 3, the operating element 16 can include a display 19 with several LEDs for displaying the intensity of the adjusted brightness of the operating lamp 1, a display 20 with several LEDs for displaying the intensity of the adjusted color temperature, a display 21 for displaying the adjustment of the operating lamp 1 for deep or shallow wounds, and a display 22 for displaying the adjustment of the operating lamp 1 for one ore more operating surgeons within the light field.

Activating can be performed, e.g., as follows:

| Situation (distribution) | Color temperature | Illumination intensity | Module 1 | | | | | Module n | | | |
|---|---|---|---|---|---|---|---|---|---|---|---|
| | | | ww | kw | bl | cn | ... | ww | kw | bl | cn |
| S1 | 3500 K | 50% | 60 | 20 | 0 | 0 | ... | 59 | 22 | 0 | 0 |
| S1 | 4000 K | 50% | 55 | 25 | 20 | 20 | ... | 53 | 27 | 22 | 19 |

-continued

| Situation (distribution) | Color temperature | Illumination intensity | Module 1 | | | | ... | Module n | | | |
|---|---|---|---|---|---|---|---|---|---|---|---|
| | | | ww | kw | bl | cn | ... | ww | kw | bl | cn |
| — | — | — | — | — | — | — | ... | — | — | — | — |
| S1 | 5500 K | 100% | 95 | 98 | 85 | 83 | ... | 96 | 99 | 83 | 84 |
| — | — | — | — | — | — | — | ... | — | — | — | — |
| — | — | — | — | — | — | — | ... | — | — | — | — |
| S4 | 5500 K | 100% | 102 | 85 | 80 | 78 | ... | 0 | 0 | 0 | 0 |

Ww = warm white
Kw = cold white
Bl = blue
Cn = cyan

What is claimed is:

1. An operating lamp comprising:
  a plurality of illumination elements arranged in a plurality of discrete groups, the illumination elements including
    at least one white illumination element adapted to emit a white light, and
    multiple colored illumination elements, each adapted to emit a non-white, colored light;
  a controller configured to communicate with the illumination elements; and
  multiple storage devices configured to communicate with the controller, each of the storage devices being associated with one or more of the groups of illumination elements, and each storage device containing a predetermined set of power values for each associated group of illumination elements,
  wherein the controller is configured to control illumination of each group of illumination elements individually based on the associated power values to produce a predetermined nominal output, the power values comprising calibrated data corresponding to a set of nominal operating values of the operating lamp, the plurality of illumination elements together defining a light emitting surface, at least one of the nominal operating values corresponding to a desired distribution of light intensity over the emitting surface, and the distribution of light intensity having a lighting characteristic that corresponds to a particular operating environment.

2. The operating lamp according to claim 1, wherein at least one of the nominal operating values is a color temperature of the operating lamp.

3. The operating lamp according to claim 1, wherein at least one of the nominal operating values is a light intensity of the operating lamp.

4. The operating lamp according to claim 1, wherein at least one of the power values corresponds to an operating current strength for a corresponding one of the associated groups of illumination elements.

5. The operating lamp according to claim 1, wherein at least one of the power values corresponds to a pulse sequence for pulse width modulation of a corresponding one of the associated groups of illumination elements.

6. The operating lamp according to claim 5, wherein the illumination elements are mounted in a plurality of lighting modules, wherein each module comprises one or more of the discrete groups of illumination elements and the associated storage devices.

7. The operating lamp according to claim 1, wherein the storage devices are selected from the group consisting of EEPROMs and flash memory devices.

8. The operating lamp according to claim 1, further comprising a user interface configured to communicate with the controller and operable to select from a plurality of discrete light intensity settings, a plurality of discrete color temperature settings, and a plurality of discrete light intensity distribution settings.

9. The operating lamp according to claim 1, wherein the power values correspond to a power at which each individual group is driven to reproduce the predetermined nominal output.

10. The operating lamp according to claim 1, wherein the operating environment comprises one operating surgeon.

11. The operating lamp according to claim 1, wherein the operating environment comprises two operating surgeons.

12. The operating lamp according to claim 1, wherein the operating environment comprises a large surface wound.

13. The operating lamp according to claim 1, wherein the operating environment comprises a deep narrow wound.

14. An illumination method comprising:
  delivering a set of calibrated power values from a storage device of each of a plurality of lighting modules to a central controller;
  individually controlling one or more illumination parameters of each of a plurality of groups of illumination elements with a corresponding set of the calibrated power values that correspond to a desired distribution of light intensity over an emitting surface, to produce an emitted light having a predetermined nominal output value, the distribution of light intensity having a lighting characteristic that corresponds to a particular operating environment; and
  illuminating an operating environment with the illuminated light.

15. The method according to claim 14, wherein the power value corresponds to a power at which each individual group is driven to produce the predetermined nominal output value.

16. The method according to claim 14, wherein the one or more illumination parameters are selected form the group consisting of: color temperature, and light intensity.

17. The method according to claim 14, wherein the illumination elements are grouped according to a color of light emitted therefrom.

18. The method according to claim 14, wherein the illumination elements comprise LEDs including:
  at least one warm white LED;
  at least one cool white LED;
  at least one cyan colored LED; and
  at least one blue colored LED.

19. A method comprising:
  arranging a plurality of illumination elements in a plurality of discrete groups, each discrete group having an associated storage device;

applying a flow of electrical current to each group of illumination elements to cause the illumination elements to emit a light;

measuring a lighting parameter of the emitted light;

adjusting the flow of electrical current to at least one of the groups such that the measured lighting parameter substantially reproduces a predetermined nominal operating value that corresponds to a desired distribution of light intensity over an emitting surface, the distribution of light intensity having a lighting characteristic that corresponds to a particular operating environment; and recording a power value for each of the plurality of discrete groups on the respective storage devices associated with the groups, wherein the recorded power value corresponds to a strength of the flow of electrical current through the associated group when the measured lighting parameter substantially reproduces the predetermined nominal operating value.

20. An operating lamp comprising:

a plurality of lighting modules each comprising:

a plurality of LEDs arranged in a plurality of discrete groups and including:

at least one warm white LED, at least one cool white LED, at least one cyan colored LED, and at least one blue colored LED; and one or more storage devices, wherein each group of illumination elements is associated with a corresponding one of the storage devices, and wherein each storage device contains a set of calibrated power values for each associated group;

a controller configured to communicate with each of the storage devices; and a user interface configured to communicate with the controller and operable to select between a plurality of discrete output settings that correspond to a desired distribution of light intensity over an emitting surface, the distribution of light intensity having a lighting characteristic that corresponds to a particular operating environment, wherein the controller is configured to control illumination of the discrete groups of LEDs individually, based on the corresponding power values in combination with input from the user interface.

21. The operating lamp according to claim 20, wherein the power values correspond to a current strength at which each individual group is driven to substantially reproduce a predetermined nominal output.

22. The operating lamp according to claim 20, wherein the power values correspond to pulse sequences for pulse width modulation of a supply current to the corresponding groups.

23. The operating lamp according to claim 20, wherein the plurality of lighting modules together define a concave light emitting surface.

24. The operating lamp according to claim 20, wherein the lighting modules are formed in the shape of hexagons connected together and forming a honeycomb structure.

25. The operating lamp according to claim 20, wherein the storage devices are EEPROMs.

* * * * *